United States Patent [19]

Prasad et al.

[11] Patent Number: 5,527,939

[45] Date of Patent: Jun. 18, 1996

[54] AMINE CATALYZED REACTION OF ALKYL MERCAPTANS WITH THIOPHOSPHORYL CHLORIDE

[75] Inventors: Vidyanatha A. Prasad; Peter E. Newallis, both of LeaWood, Kans.

[73] Assignee: Bayer Corporation, Pittsburgh, Pa.

[21] Appl. No.: 234,096

[22] Filed: Apr. 28, 1994

[51] Int. Cl.$^6$ ................................................. C07F 9/20
[52] U.S. Cl. .................................................... 558/101
[58] Field of Search ........................................ 558/101

[56] References Cited

U.S. PATENT DOCUMENTS

| | | | |
|---|---|---|---|
| 1,785,951 | 12/1930 | Gibson et al. | 558/101 |
| 3,790,649 | 2/1974 | Schumacher | 558/101 |
| 3,879,500 | 4/1975 | Uhing et al. | 260/981 |
| 3,965,220 | 6/1976 | Schumacher | 558/101 |
| 4,082,822 | 4/1978 | Diehr et al. | 260/972 |
| 4,956,487 | 9/1990 | Robbins et al. | 558/101 X |

FOREIGN PATENT DOCUMENTS 187785 10/1966 Russian Federation.

OTHER PUBLICATIONS

Kosolapoff, G. M. and Maier, L. *Organic Phosphorus Compounds;* vol. 7; John Wiley and Sons: New York, 1976; pp. 500–502.

Houben–Weyl: "Die Methoden der Organischen Chemie" (The Methods of Organic Chemistry), vol.12/2 p. 682 (1964) George Thieme Verlag Stuttgart.

*Primary Examiner*—Johann Richter
*Assistant Examiner*—Michael G. Ambrose
*Attorney, Agent, or Firm*—Joseph C. Gil; Godfried R. Akorli

[57] ABSTRACT

Disclosed herein is an improved process for preparing a phosphorodihalodithioate comprising reacting a mercaptan with a thiophorphoryl halide in the presence of a catalyst, the improvement comprising a catalytic amount of a tertiary amine catalyst.

8 Claims, No Drawings

AMINE CATALYZED REACTION OF ALKYL MERCAPTANS WITH THIOPHOSPHORYL CHLORIDE

BACKGROUND OF THE INVENTION

1. Field of the Invention

The present invention relates to an improved process for the preparation of phosphorodihalodithioates that can be used as intermediates for the synthesis of insecticidally active compounds.

2. Brief Description of the Prior Art

Disclosed by the prior art is a process for preparing phosphorodihalothioates by heating the corresponding phosphoric acid alkyl ester dichlorides with phosphorus(V) sulfide to 140°–150° C. (see Houben-Weyl: "Die Methoden der Organischen Chemie" (The Methods of Organic Chemistry), Volume 12/2, page 682 [1964], George Thieme Verlag Stuttgart). Alternately, O-alkyl ester dichlorides can be reacted directly with phosphorus(V) sulphide to give the dithiophosphoric acid alkyl ester dichlorides.

In carrying out these processes industrially, one finds problems in separating and removing the phosphorus pentoxide by-product. After separating the dithiophosphoric acid alkyl ester dichlorides, there remain solid phosphorus pentoxide and sulphur-containing, extremely malodorous compounds. Their removal to leave an odor-free product, say by oxidation in an alkaline medium, is only partially feasible, and requires long times and high costs.

Another method of preparing dithiophosphoric acid ester dichlorides comprises reacting elemental sulphur with thiophosphorous acid ester dichlorides that are obtained from the reaction of thiols and phosphorus trichloride. The reaction of sulphur with the thiophosphorous acid ester dichlorides only takes place at temperatures above 100° C. The resulting sulphurization of the thiophosphorous ester dichlorides is attended by a marked disproportionation to dithiophosphorous acid diester chlorides and phosphorus trichloride. To suppress the disproportionation, the sulphurization must be carried out under pressure (see Houben-Weyl, loc. cit.).

U.S. Pat. No. 3,879,500 and Russian Patent No. 187,785 disclose what appears to be a simple method of preparing dithiophosphoric acid ester dichlorides. The method comprises reacting corresponding thiol compounds with thiophosphoryl chloride. However, if too large an amount of thiol compound is employed in this reaction, trithiophosphoric acid diester chlorides and tetrathiophosphoric acid esters are obtained, almost exclusively as the reaction product even in the presence of acid-binding agents (see also Houben-Weyl, loc. cit.).

U.S. Pat. No. 4,082,822 discloses a process for the preparation of a dithiophosphoric acid dihalide by reacting a thiol compound with a thiophosphoryl halide in the presence of a catalyst. Distinctly, the catalyst is selected from the group consisting of a metal, an anhydrous metal halide, a Lewis acid, a nitrogen-alkylated lactam or an N,N-disubstituted carboxylic acid amide or phosphoric acid amide at a temperature of about 0° to 170° C.

DESCRIPTION OF THE INVENTION

The present invention now provides a highly efficient process for the preparation of phosphorodihalodithioates of the general formula

in which

X represents chlorine or bromine, and

R represents a straight chain or branched alkyl radical with up to 8 carbon atoms (which is optionally substituted by alkoxy or alkylthio), a cycloaliphatic radical with 5 or 6 ring members, an aralkyl radical with 6 to 8 carbon atoms, comprising reacting a mercaptan of the general formula R—SH in which R has the above-mentioned meaning, with a thiophosphoryl halide of the general formula $PSX_3$ in which X has the above-mentioned meaning, and is preferably chlorine, in the presence of a tertiary amine.

Preferably R represents alkyl with 1 to 4 carbon atoms.

The method according to the invention has a number of advantages over the known methods for the preparation of phosphorodihalodithioates. It requires easily accessible starting materials, which can be reacted in an easily regulated one-pot process, to give high yields of the desired products. The process can be used to prepare phosphorodihalodithioates with a variety of possible substituents. The phosphorodihalodithioates obtainable in accordance with the process can be isolated from the reaction mixture by simple operations, such as distillation or crystallization. A distinct feature of the invention is that the process does not pollute the environment. The by-product hydrogen halide can be removed easily and the catalysts can be recycled repeatedly. Hence, it is not necessary to discharge the catalysts from the reaction vessel after they have been used once.

The mercaptans which according to the invention can be used as starting materials are known and can be prepared, for example, in accordance with the methods described in Houben-Weyl, op. cit., Volume IX, page 3 et seq. Preferably, the mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan. More preferably, the mercaptan is propyl mercaptan.

The catalysts that are useful herein are base catalysts which are typically amines. The amines can be selected from the group consisting of 2-methyl-5-ethylpyridine, 2-methylpyridine, 2,4-dimethyl-pyridine, 2,6-dimethylpyridine, 2,4,6-trimethylpyridine, tri-n-propylamine, tri-n-butylamine. Preferred herein as the catalyst are 2-methyl-5-ethylpyridine and tri-n-butylamine.

The use of a solvent or diluent when carrying out the process is not necessary, but halogenated hydrocarbons, such as monochlorobenzene or dichlorobenzene, can be employed.

In carrying out the process according to the invention, about 1.1 to 2, preferably about 1.4 to 1.9 moles of thiophosphoryl halide and about 0.001 to 0.1, preferably about 0.005 to 0.1 mole of catalyst are employed per mole of the mercaptan. In a preferred embodiment of the invention, n-propylmercaptan and thiophosphoryl chloride are used as starting materials. The reaction can be conducted at initial temperatures of about 50° C. to 80° C. and preferably 55° C. to 60° C. and a final temperature of 140° to 150° C.

The process for the preparation of the phosphorodihalodithioates which are to be purified by distillation can therefore be carried out by recycling the heel containing catalyst. After completion of the reaction and after distilling the excess thiophosphoryl halide and the phosphorodihalodithioates, the distillation heel which contains the catalyst, is again reacted with thiophosphoryl halide and the mercaptan without adding a substantial amount of fresh catalyst.

The method of working up of a reaction mixture depends on the physical properties of the phosphorodihalodithioates. In general, phosphorodihalodithioates are liquid and can be separated by distillation under reduced pressure.

As can be seen from the foregoing, the process of the invention can be characterized by the advantage of using a tertiary amine catalyst which produces a fluid heel on distillation of the reaction mixture. The phosphorodihalodithioates which can be prepared by the process according to the invention may be used as intermediates for the synthesis of insecticidal thiophosphoric acid esters.

The invention is further illustrated but is not intended to be limited by the following examples in which all parts and percentages are by weight unless otherwise specified.

EXAMPLES

Example 1
Synthesis of n-Propylphosphorodichloridodithioate via the Reaction of n-Propylmercaptan with PSCl$_3$ Catalyzed by 2-Methyl-5-ethylpyridine

| Charges: | | |
|---|---|---|
| PSCl$_3$: | 169.4 g | (1.0 mol) |
| 2-Methyl-5-ethylpyridine: | 1 g | |
| n-Propylmercaptan: | 76.16 g | (1.0 mol) |

Procedure:

To a 1,000 ml 4-necked round bottomed flask, fitted with an overhead stirrer, thermometer, addition funnel, brine cooled condenser (–5° C.), NaOH scrubber system and a nitrogen inlet line, was charged 169.4 g (1.0 mol) of PSCl$_3$ and 1 g of 2-Methyl-5-ethylpyridine. To the well agitated PSCl$_3$ was charged a mixture of "heels" (100 g) from previously produced batches of ester dichloride and the temperature raised gradually to 55°–60° C. To this reaction mixture was added 76.16 g (1.0 mol) of n-Propylmercaptan over a period of 1 hour using a gentle nitrogen flow. The final ratio of moles of PSCl$_3$ to moles of n-Propylmercaptan was 1.52; the additional PSCl$_3$ being supplied by the "heels" recycled from the previous batch. The reaction temperature was gradually raised to 145° C. and the mixture cooked at this temperature for 4 hours.

The reaction mixture was subjected to vacuum distillation (10 mmHg). A forecut (mostly PSCl$_3$) was collected over a temperature range of 25°–79° C. a main cut was collected over a temperature range of 95°–110° C. and it analyzed 90% ester dichloride. A heel residue comprising

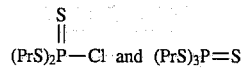

as the main constituents was saved for the next batch. The crude product was further refined via vacuum distillation as 10 mmHg. PSCl$_3$ and Dipropyldisulfide were collected as fore-cuts, the ester dichloride was collected as the main-cut while the higher boiling components were retained in the "heel". The forecuts and the "heel" residues were all combined for recycle to the subsequent batch.

The distilled product analyzed 96.5% active ingredient (by gas/liquid chromatography) and contained 0.5% PSCl$_3$, 0.3% dipropyldisulfide, and 0.7%.

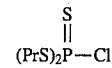

as the main impurities.

This process was repeated over 15 batches using no additional 2-Methyl-5-ethylpyridine in subsequent batches. The yield of distilled product, over 15 batches, amounted to 94.5% based on Propylmercaptan charged.

Examples 2–5

In the following examples, there were employed essentially the same procedure and evaluation as described in Example 1. The results are listed in the following tables.

| Catalyst | Run No. | % K-500 | % DPDS | % Yield on PrSH | Purity |
|---|---|---|---|---|---|
| 2-methyl 5-ethyl pyridine | 1 | 45.5 | 0.3 | 82.5 | Ca. 97% |
| | 2 | 55.0 | 0.4 | 93.5 | |
| | 3 | 61.5 | 0.3 | 95.5 | |
| | 4 | 61.5 | 0.3 | 96.5 | |
| Tributylamine | 1 | 52.2 | 0.3 | 83.1 | 97.5% |
| | 2 | 60.1 | 0.2 | 91.8 | |
| | 3 | 61.2 | 0.2 | 95.5 | |
| | 4 | 62.5 | 0.2 | 97.1 | |
| 2,4-Lutidine | 1 | 46.5 | 0.4 | 81.5 | 97.0% |
| | 2 | 56.2 | 0.4 | 92.5 | |
| | 3 | 61.5 | 0.3 | 94.5 | |
| | 4 | 61.5 | 0.4 | 96.5 | |
| 2,6-Lutidine | 1 | 45.2 | 0.4 | 81.8 | 97.0% |
| | 2 | 57.1 | 0.4 | 92.6 | |
| | 3 | 61.3 | 0.4 | 94.3 | |
| | 4 | 61.8 | 0.3 | 96.1 | |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An improved process for preparing a phosphorodihalidodithioate comprising reacting a mercaptan with a thiophosphoryl halide in the presence of a catalyst, the improvement comprising a catalytic amount of a tertiary amine catalyst selected from the group consisting of 2-methyl-5-ethylpyridine, 2-methylpyridine, 2,4-dimethylpyridine, 2,6-dimethylpyridine, 2,4,6-trimethylpyridine, tri-n-propylamine, and tri-n-butylamine.

2. The process of claim 1 wherein the amine is 2-methyl-5-ethylpyridine.

3. The process of claim 1 wherein the amine is tri-n-butylamine.

4. The process of claim 1 wherein the mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan.

5. The process of claim 4 wherein the mercaptan is n-propyl mercaptan.

6. The process of claim 1 wherein the halide is a chloride.

7. The process of claim 1 further comprising distilling the phosphorodihalodithioate and a by-product thiophosphoryl halide to provide a fluid distillation heel containing catalyst.

8. A process of claim 7 comprising reacting the distillation heel with a mercaptan and thiophosphoryl halide without a substantial addition of fresh catalyst.

* * * * *